US012741992B2

(12) United States Patent
Boenitz-Dulat et al.

(10) Patent No.: US 12,741,992 B2
(45) Date of Patent: Sep. 22, 2026

(54) BACTERIAL PILUS PROTEIN COMPLEX FIMGT-DSF STABILIZED PROTEIN COMPLEXES FOR PRODUCING FILAMENTOUS PHAGES

(71) Applicant: Roche Diagnostics Operations, Inc., Indianapolis, IN (US)

(72) Inventors: Mara Boenitz-Dulat, Penzberg (DE); Michael Schraeml, Penzberg (DE); Bigna Woersdoerfer, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 661 days.

(21) Appl. No.: 18/028,245

(22) PCT Filed: Sep. 28, 2021

(86) PCT No.: PCT/EP2021/076623
§ 371 (c)(1),
(2) Date: Mar. 24, 2023

(87) PCT Pub. No.: WO2022/069461
PCT Pub. Date: Apr. 7, 2022

(65) Prior Publication Data

US 2023/0382957 A1 Nov. 30, 2023

(30) Foreign Application Priority Data

Sep. 30, 2020 (EP) .................................... 20199192

(51) Int. Cl.
*C07K 14/245* (2006.01)
*C12N 15/10* (2006.01)

(52) U.S. Cl.
CPC ........ *C07K 14/245* (2013.01); *C12N 15/1037* (2013.01); *C07K 2319/70* (2013.01)

(58) Field of Classification Search
None
See application file for complete search history.

(56) References Cited

U.S. PATENT DOCUMENTS

| | | | |
|---|---|---|---|
| 9,803,191 | B2 | 10/2017 | Tesar et al. |
| 2012/0270241 | A1 | 10/2012 | Bryan |

FOREIGN PATENT DOCUMENTS

| | | | |
|---|---|---|---|
| JP | 2013-510559 | A | 3/2013 |
| JP | 2015-521852 | A | 8/2015 |
| WO | 1998019705 | A1 | 5/1998 |
| WO | 2012028697 | A1 | 3/2012 |
| WO | 2017148862 | A1 | 9/2017 |
| WO | 2018041740 | A1 | 3/2018 |

OTHER PUBLICATIONS

Giese et al. The Most Stable Protein-Ligand Complex: Applications for One-Step Affinity Purification and Identification of Protein Assemblies. Angew. Chem. Int. Ed. 2012, 51: 4474-4478.*

Jespers et al., Surface Expression and Ligand-Based Selection of cDNAs Fused to Filamentous Phage Gene VI, Bio/Technology, vol. 13, 1995, pp. 378.

Velappan et al., A comprehensive analysis of filamentous phage display vectors for cytoplasmic proteins: an analysis with different fluorescent proteins, Nucleic Acid Res., vol. 38, No. 4, 2010, pp. e22.

Fuh et al., (2000), Efficient phage display of polypeptides fused to the carboxy-terminus of the M13 gene-3 minor coat protein, FEBS Letters, 480, doi: 10.1016/S0014-5793(00)01946-3.

Held et al., Comprehensive Mutational Analysis of the M13 Major Coat Protein: Improved Scaffolds for C-terminal Phage Display, J Mol Biol., vol. 340, No. 3, 2004, pp. 587.

Freudl: "Signal peptides for recombinant protein secretion in bacterial expression systems", Microb Cell Fact, vol. 17, 2018, pp. 52, Retrieved from the Internet <URL:https://doi.org/10.1186/sl2934-018-0901-3>.

Green et al., "Bacterial Secretion Systems: An Overview", Microbiology Spectrum, vol. 4, Nr.: 1, Feb. 2, 2016.

Han et al.: "Novel signal peptides improve the secretion of recombinant *Staphylococcus aureus* Alpha toxinH35L in *Escherichia coli*", AMB Express, vol. 7, No. 1, 2017, pp. 93.

Puorger et al., Infinite Kinetic Stability against Dissociation of Supramolecular Protein Complexes through Donor Strand Complementation, Structure, vol. 16, 2008, pp. 631.

Giese et al., "Accelerating the Association of the Most Stable Protein-Ligand Complex by More than Two Orders of Magnitude", Angew. Chem., vol. 55, 2016, pp. 9350.

Chen et al., "Fusion protein linkers: Property, design and functionality", Adv Drug Deliv Rev. 2013;65(10): 1357-1369. doi: 10.1016/j.addr.2012.09.039.

Klein et al., Design and characterization of structured protein linkers with differing flexibilities, Protein Engineering, Design and Selection, vol. 27, Issue 10, Oct. 2014, pp. 325-330, https://doi.org/10.1093/protein/gzu043.

Brunetti et al., Branched peptides as bioactive molecules for drug design. Pept Sci. 2018; 110:e24089. https://doi.org/10.1002/pep2.24089.

Hopp et al., A Short Polypeptide Marker Sequence Useful for Recombinant Protein Identification and Purification. Nat Biotechnol 6, 1204-1210 (1988). https://doi.org/10.1038/nbtl088-1204.

Kimple et al.. Overview of affinity tags for protein purification. Curr Protoc Protein Sci. 2013;73 :9.9.1-9.9.23. Published Sep. 24, 2013. doi: 10.1002/0471140864. ps0909s73.

Qi et al., Phagemid vectors for phage display: properties, characteristics and construction. J Mol Biol. 2012; 417(3):129-143. doi:10.1016/j.jmb.2012.01.038.

Boriana Marintcheva, Harnessing the Power of Viruses, Academic Press, 2018, Chapter 5, pp. 133-160, ISBN 9780128105146, https://doi.org/10.1016/B978-0-12- 810514-6.00005-2.

(Continued)

*Primary Examiner* — Nianxiang Zou
(74) *Attorney, Agent, or Firm* — Taft Stettinius & Hollister LLP

(57) ABSTRACT

The present invention relates to bacterial pilus protein complex FimGt-DsF stabilized protein complexes for producing phagemids or filamentous phages, and methods for use of these.

18 Claims, 5 Drawing Sheets

Figure 1:
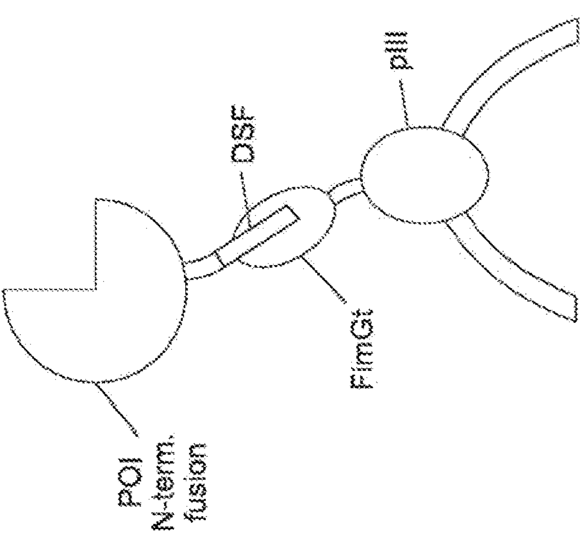
Figure 1:
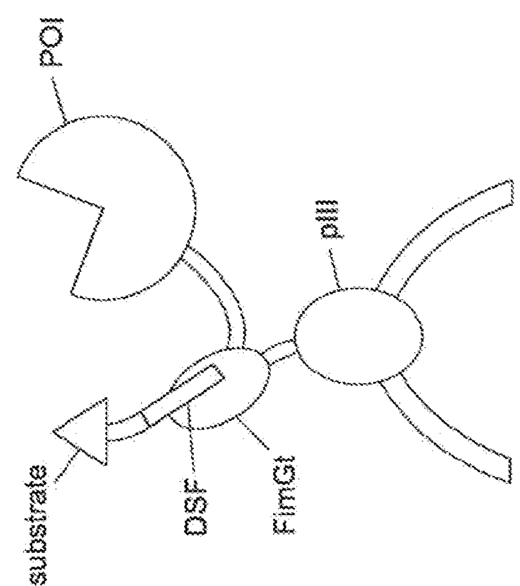

Specification includes a Sequence Listing.

(56) References Cited

OTHER PUBLICATIONS

International Preliminary Report on Patentability; The International Bureau of WIPO; International Application No. PCT/EP2021/076623; Mar. 28, 2023; 8 pages.
Crameri et al., Display of biologically active proteins on the surface of filamentous phages: a cDNA cloning system for selection of functional gene products linked to the genetic information responsible for their production, Gene, 1993, vol. 137, pp. 69-75.
Demartis et al., A Strategy for the Isolation of Catalytic Activities from Repertoires of Enzymes Displayed on Phage, J. Mol. Biol., 1999, vol. 286 , pp. 617-633.
Japanese Office Action, Japan Patent Office, Japanese Patent Application No. 2023-419611, Apr. 30, 2024, 11 pages.
International Search Report and Written Opinion of the International Searching Authority: European Patent Office; International Application No. PCT/EP2021/076623; Dec. 21, 2021; 16 pages.
Giese, Christoph et al.; The Most Stable Protein-Ligand Complex: Applications for One-Step Affinity Purification and Identification of Protein Assemblies; Angewandte Communications; 2012; pp. 4474-4478; vol. 51.
Bowley, D.R. et al.; Antigen selection from an HIV-1 immune antibody library displayed on yeast yields many novel antibodies compared to selection from the same library displayed on phage; Protein Engineering, Design & Selection; 2007; pp. 81-90; vol. 20, No. 2.

* cited by examiner

A

B

HisPol-pIII before selection 1 antibody Fab
2 Fim_PelB
3 Fim_DsbA
4 Fim_TorA
5 No Fim_PelB
6 No Fim_DsbA
7 No Fim_TorA after selection 1 antibody Fab
2 Fim_PelB
3 Fim_DsbA
4 Fim_TorA
5 No Fim_PelB
6 No Fim_DsbA
7 No Fim_TorA after control selection w/o DNA 1 antibody Fab
2 Fim_PelB
3 Fim_DsbA
4 Fim_TorA
5 No Fim_PelB
6 No Fim_DsbA
7 No Fim_TorA

BACTERIAL PILUS PROTEIN COMPLEX FIMGT-DSF STABILIZED PROTEIN COMPLEXES FOR PRODUCING FILAMENTOUS PHAGES

CROSS-REFERENCE TO RELATED APPLICATIONS

This application is a U.S. National Phase of International PCT Application No. PCT/EP2021/076623 filed on Sep. 28, 2021, which claims priority to European Patent Application No. 20199192.4 filed on Sep. 30, 2020, the contents of each application are incorporated herein by reference in their entireties.

The present invention relates to bacterial pilus protein complex FimGt-DsF stabilized protein complexes for producing phagemids or filamentous phages, and methods for use of these.

BACKGROUND OF THE INVENTION

Phage display is a powerful method for the selection of improved binders. Phage display work often involves use of the filamentous phage M13 that infects *Escherichia coli* due to the relative ease of working with M13 compared to other phages. Filamentous phages like M13 do not lyse the host cells but am instead released by secretion. This allows simpler and more efficient purification of the phage particles from potentially interfering cytoplasmic proteins. Display of the polypeptide of interest (POI) on M13 is most commonly achieved by fusion to the N-terminus of the minor coat protein pIII, but fusion to the other coat proteins (pVI, pVII, pVIII and pIX) has also been used.

Phage display has been extensively utilized for the successful selection of antibody and peptide libraries. However, conventional phage display exhibits some limitations hampering its broader use. One shortcoming is the lack of robust N-terminal display (defined as display via attachment of the N-terminus of the POI) for applications not suitable for C-terminal display, such as the display of proteins requiring a free C-terminus for interaction, display of cDNA libraries and proteins not tolerant to C-terminal fusion.

WO 2018/041740 discloses a non-covalent display system for use of immobilization of proteins on the surface of cells, comprising a protein of interest (POI) fused to a first binding moiety wherein the first binding moiety comprises one partner of the FimGT/DsF interaction pair.

WO 2012/028697 discloses a system based on donor strand (Ds) complementation comprising a Ds-tag and a cognate ligand of the Ds-tag as protein tags and affinity ligands for use in immobilization and/or affinity purification procedures.

Giese et al. (in: "The Most Stable Protein-Ligand Complex: Applications for One-Step Affinity Purification and Identification of Protein Assemblies", ANGEWANDTE CHEMIE INTERNATIONAL EDITION, vol. 51, no. 18, 27 Apr. 2012, pages 4474-4478) disclose the use of the FimGT/DsF system for one step affinity purification and identification of protein assemblies.

N-terminal fusion of proteins to the C-terminus of pIII, pVI, pVIII, and pIX has been shown, but resulted in low display levels (Jespers et al. Bio/Technology 1995, 13, 378; Velappan et al., Nucleic Acid Res 2010, 38, 4, e22), and was successful or successfully shown only with peptides or small proteins (Fuh et al. FEBS Letters 2000, 480, 231; Fuh, Germaine and Sidhu, Sachdev S. (2000), Efficient phage display of polypeptides fused to the carboxy-terminus of the M13 gene-3 minor coat protein, FEBS Letters, 480, doi: 10.1016/S0014-5793(00)01946-3; 25 Velappan et al. Nucleic Acid Res. 2010, 38, 4, e22), and/or required tailored optimization (Held et al., 3 Mol Biol. 2004, 340(3), 587).

It is therefore an object of the present invention to provide improved stabilized protein complexes for producing phagemids or filamentous phages, and methods for the production and use of these Other objects and advantages will become apparent to the person of skill when studying the present description of the present invention.

In a first aspect of the present invention, the above object is solved by providing a protein complex comprising a) a first polypeptide chain having the general formula (I) in N- to C-terminal direction X-DsF-Y-POI (1), and b) a second polypeptide chain having the general formula (II) in N- to C-terminal direction X-FimGt-Y-CPF (II), wherein X is absent or designates a bacterial leader sequence or translocation sequence, DsF designates a bacterial DsF-polypeptide required for binding to FimGt or a bacterial homolog thereof, Y is absent or designates at least one of a linker sequence, a detectable peptide sequence and/or a peptide sequence for purifying said polypeptide chain, POI designates a protein of interest, FimGt designates a bacterial FimGt-polypeptide required for binding to DsF or a bacterial homolog thereof, and CPF designates a coat protein of a filamentous phage.

In a second aspect of the present invention, the above object is solved by providing a protein complex comprising a) a first polypeptide chain having the general formula (111) in N- to C-terminal direction X-SUB-DsF-Y (III), and b) a second polypeptide chain comprising at least one POI and having the general formula (IV) in N- to C-terminal direction X-FimGt(POI)-Y(POI)-CPF (IV), wherein X is absent or designates a bacterial leader sequence or translocation sequence, DsF designates a bacterial DsF-polypeptide required for binding to FimGt or a bacterial homolog thereof, Y(POI) is absent or designates at least one of a branched linker sequence having POI attached thereto, a detectable peptide sequence and/or a peptide sequence for purifying said polypeptide chain, POI designates a protein of interest, FimGt(POI) designates a bacterial FimGt-polypeptide required for binding to DsF or a bacterial homolog thereof, optionally having POI linked thereto, SUB designates a substrate or ligand, and CPF designates a coat protein of a filamentous phage.

Advantageously, the protein complex according to the present invention is stabilized or essentially stabilized through donor strand complementation between the independent contiguous polypeptide sequences of formula I and II, and formula III and IV, respectively.

In a third aspect of the present invention, the above object is solved by providing a filamentous phage displaying at least one protein of interest (POI), comprising the protein complex according to the present invention. Preferred is a library of the filamentous phage according to the present invention, displaying variants of POI and/or the substrate and/or ligand (SUB).

In a fourth aspect of the present invention, the above object is solved by providing a nucleic acid encoding for the first or second polypeptide chain of the protein complex according to the present invention, or a nucleic acid encoding for the first or second polypeptide chain of the protein complex according to the present invention. Preferred is a bicistronic nucleic acid encoding the first and second polypeptide chain of the protein complex according to the present invention, or a bicistronic nucleic acid encoding the first and second polypeptide chain of the protein complex according to the present invention. Further preferred is a library of nucleic acids according to the present invention.

In a fifth aspect of the present invention, the above object is solved by providing a phagemid comprising a nucleic acid according to the present invention or a library of phagemids comprising nucleic acids according to the present invention.

In a sixth aspect of the present invention, the above object is solved by providing a method for producing a phagemid according to the present invention, or for producing a library of phagemids according to the present invention, as disclosed herein.

In a seventh aspect of the present invention, the above object is solved by providing a method for producing a filamentous phage according to the present invention, or for producing a library of filamentous phages according to the present invention, as disclosed herein.

In an eighth aspect of the present invention, the above object is solved by providing a method for screening for a protein of interest (PO) that specifically interacts with a subs-rate or ligand, comprising a) Providing a phage library according to the present invention, b) Contacting said substrate or ligand to said library of a), c) Determining an interaction, preferably a specific interaction, of said substrate or ligand with said library, and d) Identifying a POI based on said interaction, preferably said specific interaction. Preferably, said PO is an antibody or fragment thereof, and said method comprises biopanning or said POI is a polymerase or truncated version thereof.

In an ninth aspect of the present invention, the above object is solved by the use of the protein complex according to the present invention, the nucleic acid according to the present invention or the library of nucleic acids according to the present invention for producing phagemids or filamentous phages as disclosed herein.

As mentioned above, in a first aspect thereof, the present invention relates to a protein complex comprising a first polypeptide chain having the general formula (I) in N- to C-terminal direction X-DsF-Y-POI (I), and a second polypeptide chain having the general formula (II) in N- to C-terminal direction X-FimGt-Y-CPF (II).

It was surprisingly found that a suitable functional phage display of the PO (e.g. a DNA polymerase) is dependent from its attachment to the phage. When fused at its C-terminus, the POI greatly loses activity; this was not observed when an N-terminal fusion was used.

In formula I and II, X is absent or designates a bacterial leader sequence or translocation sequence. Preferably, said bacterial leader or translocation sequence is selected from a leader sequence for secretion by a secretion pathway or a translocation sequence for translocation by a translocation system, such as, for example, PelB, DsbA, TorA, and PhoA, and the general secretion (Sec) pathway, twin arginine translocation (Tat) pathway, T2SS pathway, T3SS pathway, T5SS pathway, and SecA2 pathway. Suitable signal sequences and the design thereof can be based on the respective literature and the knowledge of the skilled person, for example, Sec and Tat signal peptides possess a similar tripartite overall structure consisting of a positively charged n-region, a central hydrophobic h-region, and a polar c-region that contains the recognition site (consensus: A-X-A) for signal peptidase (SPase; the cleavage site is indicated by an arrow). In Tat signal peptides, a characteristic amino acid consensus motif including two highly conserved arginine residues (underlined) is present at the boundary between the often significantly longer n-region and the h-region. Furthermore, the h-region of Tat signal peptides is mostly less hydrophobic than those found in Sec signal peptides and in the c-region of Tat signal peptides, frequently positively charged amino acids (the so-called Sec-avoidance motif) are present that prevent a mistargeting of Tat substrates into the Sec pathway (see, e.g., Freudl, R. Signal peptides for recombinant protein secretion in bacterial expression systems. *Microb Cell Fact* 17, 52 (2018) https/doi.org/10.1186/s12934-018-0901-3, and Green E R, Mecsas J. Bacterial Secretion Systems: An Overview. *Microbiol Spectr.* 2016; 4(1): 10.1128/microbiolspec. VMBF-0012-2015. doi: 10.1128/microbiolspec. VMBF-0012-2015). The signal peptides can also be muted and optimized for the host (see, e.g., Han S, Machhi S, Berge M, Xi G, Linke T, Schoner R. Novel signal peptides improve the secretion of recombinant *Staphylococcus aureus* Alpha toxin$_{H35L}$ in *Escherichia coli. AMB Express.* 2017; 7(1):93. doi:10.1186/s13568-017-0394-1).

The present invention makes use of the infinite kinetic stability of the bacterial pilus protein complex FimGt-DsF, which shows an extrapolated dissociation half-life of $3\times10^9$ years (Puorger et al., Structure 2008, 16, 631). Using FimGt-DsF for phage display in this embodiment overcomes the herein described limitations of conventional phage display by providing an extremely stable and specific linkage that enables the attachment of the POI via its N-terminus and the independent translocation of the POI and phage protein with combinations of signal sequences for the different secretion pathways.

In formula I and II, FimGt designates a bacterial FimG-polypeptide (bacterial type 1 pilus subunit FimG) required for binding to DsF or a bacterial homolog thereof, and DsF (N-terminal extension (termed donor strand, Ds) of the partner subunit FimF) designates a bacterial DsF-polypeptide required for binding to FimG, FimGt or a bacterial homolog thereof. Preferably, said bacterial DsF- and FimGt polypeptides are derived from *E. coli* or are selected from homologs of DsF and/or FimGt derived from a Gram-negative bacterium, in particular of an Enterobacteriaceae.

The term FimGt shall include the full length sequence of FimG or a bacterial homolog thereof, as well as FimG variants, in particular variants showing improved binding (see below), such as the N-terminal deletion variant of residues 1-12 truncated, optionally with the substitution Q134E. The sequence of FimG (*E. coli*) can be found in UniProtKB, Acc No: P08190.

The term DsF shall include the full length sequence of FimF or a bacterial homolog thereof, as well as FimF variants, in particular variants showing improved binding (see below), such as the peptide SRIRIRGYVR (SEQ ID NO: 1, amino acids 25 to 34. T to R exchanges underlined). The sequence of FimF (*E. coli*) can be found in UniProtKB, Acc No: P08189.

The complex between the bacterial type 1 pilus subunit FimG and the peptide corresponding to the N-terminal extension (termed donor strand, Ds) of the partner subunit FimF (DsF) exhibits a slow association rate of 330 $m^{-1}$ $s^{-1}$ that limits technical applications, such as its use in affinity purification. Structure-based approaches can be used to design pairs of FimGt (a FimG variant lacking its own N-terminal extension) and DsF variants with enhanced electrostatic surface complementarity. Association of the best mutant FimGt/DsF pairs was thus accelerated by more than two orders of magnitude, while the dissociation rates and 3D structures of the improved complexes remained essentially unperturbed. A $K_D$ value of $8.8\times10^{-22}$ m was obtained for the best mutant complex, which is the lowest value reported to date for a protein/ligand complex (C. Giese, J. Eras, A. Kern, M. A. Schärer, G. Capitani, R. Glockshuber, Accelerating the Association of the Most Stable Protein-Ligand Complex by More than Two Orders of Magnitude *Angew. Chem. Int. Ed.* 2016, 55, 9350).

In the context of the present invention, a "homolog" of a polypeptide shall mean a polypeptide that performs the same or essentially the same function, preferably binding, compared with the initial polypeptide (for example, functional FimG or FimGt and/or DsF or length variants thereof that bind to each other), and exhibits an amino acid sequence identity of at least 80%, preferably at least 90%, and more preferred of at least 95%.

In formula I and II, Y is absent or designates at least one of a linker sequence, a detectable peptide sequence and/or a peptide sequence for purifying said polypeptide chain.

Linkers are short peptide sequences that occur between protein domains, e.g. fused domains. Preferred are branched or unbranched peptide linker sequences, such as a branched or unbranched glycine or glycine/serene containing peptide linker sequence. Usually, linker sequences are introduced in order to connect and/or to provide a space between functional elements of a polypeptide construct. Linkers are often composed of flexible residues like glycine and serine so that the adjacent protein domains are free to move relative to one another Longer linkers are used when it is necessary to ensure that two adjacent domains do not sterically interfere with one another. Peptide linker sequences may also include cleavable (e.g. peptidase or chemically cleavable) linkers. Suitable linkers can be designed based on the literature and the skill of the person in the art (see, for example, Chen X, Zaro J L, Shen W C. Fusion protein linkers: property, design and functionality. *Adv Drug Deliv Rev.* 2013; 65(10):1357-1369. doi:10.1016/j.addr.2012.09.039; Joshua S. Klein, Siduo Jiang, Rachel P. Galimidi, Jennifer R. Keeffe, Pamela J. Bjorkman, Design and characterization of structured protein linkers with differing flexibilities, *Protein Engineering, Design and Selection*, Volume 27, Issue 10, October 2014, Pages 325-330, https://doi.org/10.1093/protein/gzu043). As an example as described below, a polymerase gene is fused to the truncated pIII protein via a 23 amino acid long linker. WO/1998/019705 discloses branched peptide linkers. Similarly, suitable branched linkers can also be designed based on the literature and the skill of the person in the art (see, for example, Brunetti, J. Falciani, C, Bracci, L, Pini, A. Branched peptides as bioactive molecules for drug design. *Pept Sci.* 2018; 110:e24089. https://doi.org/10.1002/pep2.24089).

Detectable peptide sequences (also designated as tags or markers) allow for the identification of said peptide sequences, and, as a consequence, of the whole fusion construct or the part thereof comprising said sequence(s) Some detectable sequences may also be used to (affinity) purify said fusion construct or the part thereof comprising said sequence. Examples are the myc-tag or the Tie2-tag to be detected with respective antibodies, other antigen markers (see, for example, Hopp, T., Prickett, K., Price, V. et al. A Short Polypeptide Marker Sequence Useful for Recombinant Protein Identification and Purification. *Nat Biotechnol* 6, 1204-1210 (1988). https://doi.org/10.1038/nbt1088-1204), chelator groups (metals, radionuclides), or fluorophore groups.

Peptide sequences for purifying the polypeptide chain of the whole fusion construct or a part thereof comprising said sequence(s) are described in the literature and known to the person of skill in the art Examples are sequences that may be used to (affinity) purify said polypeptide chain (see, for example, Kimple M E, Brill A L, Pasker R L. Overview of affinity tags for protein purification. *Curr Protoc Protein Sci.* 2013; 73.9.9.1-9.9.23 Published 2013 Sep. 24. doi:10.1002/0471140864.ps0909s73), a calmodulin binding peptide, a His-tag, such as a 6 His-tag, and/or maltose binding protein sequence.

In formula II, POI designates a protein of interest. In the polypeptide chain according to the present invention, POI can be selected from the group consisting of enzymes, antibodies and fragments thereof, such as scFvs, Fab, polymerases, such as nucleic acid polymerases, cytokines, and functional fragments thereof, and libraries or panels thereof. Preferred are antibodies and fragments thereof, nucleic acid polymerases or enzymes that cleave or modify a substrate or ligand, preferably SUB (see below), either alone or in the context with other proteins, e.g. to be screened (see also below). The cleaved or modified substrate may be detected further.

Finally, in formula II, CPF designates a coat protein of a filamentous phage, preferably a minor coat protein Examples are selected from minor coat proteins of phage fd, M13, f1, and Pf1, such as pIII, pVI, pVII, pVIII, pIX, and truncated versions thereof capable of functionally replacing the respective coat protein of a filamentous phage.

In a second aspect thereof, the present invention relates to a protein complex comprising a first polypeptide chain having the general formula (III) in N- to C-terminal direction X-SUB-DsF-Y (III), and a second polypeptide chain comprising at least one POI and having the general formula (IV) in N- to C-terminal direction X-FimGt(POI)-Y(POI)-CPF (IV).

In formula III and IV, X is absent or designates a bacterial leader sequence or translocation sequence. Preferably, said bacterial leader or translocation sequence is selected from a leader sequence for secretion by a secretion pathway or a translocation sequence for translocation by a translocation system, such as, for example, PelB, DsbA, TorA, and PhoA, and the general secretion (Sec) pathway, twin arginine translocation (Tat) pathway, T2SS pathway, T3SS pathway, T5SS pathway, and SecA2 pathway. Suitable signal sequences and the design thereof can be based on the respective literature and the knowledge of the skilled person, for example, Sec and Tat signal peptides possess a similar tripartite overall structure consisting of a positively charged n-region, a central hydrophobic h-region, and a polar c-region that contains the recognition site (consensus: A-X-A) for signal peptidase (SPase, the cleavage site is indicated by an arrow). In Tat signal peptides, a characteristic amino acid consensus motif including two highly conserved arginine residues (underlined) is present at the boundary between the often significantly longer n-region and the h-region. Furthermore, the h-region of Tat signal peptides is mostly less hydrophobic than those found in Sec signal peptides and in the c-region of Tat signal peptides, frequently positively charged amino acids (the so-called Sec-avoidance motif) are present that prevent a mistargeting of Tat substrates into the Sec pathway (see, e.g., Freudl, R. Signal peptides for recombinant protein secretion in bacterial expression systems. *Microb Cell Fact* 17, 52 (2018) https://doi.org/10.1186/s12934-018-0901-3, and Green E R, Mecsas J. Bacterial Secretion Systems: An Overview. *Microbiol Spectr.* 2016; 4(1): 10.1128/microbiolspec VMBF-0012-2015. doi:10.1128/microbiolspec VMBF-0012-2015). The signal peptides can also be muted and optimized for the host (see, e.g., Han S, Machhi S, Berge M. Xi G, Linke T, Schoner K. Novel signal peptides improve the secretion of recombinant *Staphylococcus aureus* Alpha toxin$_{H35L}$ in *Escherichia coli. AMB Express.* 2017; 7(1):93. doi:10.1186/s13568-017-0394-1).

Also in this aspect, the present invention makes use of the infinite kinetic stability of the bacterial pilus protein complex FimGt-DsF, which shows an extrapolated dissociation half-life of $3\times10^9$ years (Puorger et al, Structure 2008, 16, 631). Using FimGt-DsF for phage display in this embodiment overcomes the above described limitations of conventional phage display by providing an extremely stable and specific linkage that surprisingly enables independent translocation of the POI and phage protein with combinations of signal sequences for the different secretion pathways and the attachment of substrates for the directed evolution of bond-forming and bond-breaking enzymes.

In formula III and IV, FimGt designates a bacterial FimG-polypeptide (bacterial type I pilus subunit FimG) required for binding to DsF or a bacterial homolog thereof, and DsF (N-terminal extension (termed donor strand, Ds) of the partner subunit FimF) designates a bacterial DsF-polypeptide required for binding to FimG, FimGt or a bacterial homolog thereof. Preferably, said bacterial DsF- and FimGt polypeptides are derived from *E. coli* or are selected from homologs of DsF and/or FimGt derived from a Gram-negative bacterium, in particular of an Enterobacteriaceae.

The term FimGt shall include the full length sequence of FimG or a bacterial homolog thereof, as well as FimG variants, in particular variants showing improved binding (see below), such as the N-terminal deletion variant of residues 1-12 truncated, optionally with the substitution Q134E. The sequence of FimG (*E. coli*) can be found in UniProtKB, Acc No: P08190.

FimGt(POI) designates the bacterial FimGt-polypeptide required for binding to DsF or a bacterial homolog thereof, optionally having PO linked thereto. Linking can be done directly or indirectly by a branched or unbranched linker as described herein between the two polypeptides. e.g. FimGt-Y-(POI).

The term DsF shall include the full length sequence of FimF or a bacterial homolog thereof, as well as FimF variants, in particular variants showing improved binding (see below), such as the peptide SRIRIRGYVR (SEQ ID NO: 1, amino acids 25 to 34, T to R exchanges underlined). The sequence of FimF (*E. coli*) can be found in UniProtKB, Acc No: P08189.

The complex between the bacterial type 1 pilus subunit FimG and the peptide corresponding to the N-terminal extension (termed donor strand, Ds) of the partner subunit FimF (DsF) exhibits a slow association rate of 330 $m^{-1}$ $s^{-1}$ that limits technical applications, such as its use in affinity purification. Structure-based approaches can be used to design pairs of FimGt (a FimG variant lacking its own N-terminal extension) and DsF variants with enhanced electrostatic surface complementarity. Association of the best mutant FimGt/DsF pairs was thus accelerated by more than two orders of magnitude, while the dissociation rates and 3D structures of the improved complexes remained essentially unperturbed. A $K_D$ value of $8.8\times10^{-22}$ m was obtained for the best mutant complex, which is the lowest value reported to date for a protein/ligand complex (C. Giese, J. Eras, A. Kern, M. A. Schärer, G. Capitani, R. Glockshuber, Accelerating the Association of the Most Stable Protein-Ligand Complex by More than Two Orders of Magnitude *Angew. Chem. Int. Ed,* 2016, 55, 9350).

Also in this context of the present invention, a "homolog" of a polypeptide shall mean a polypeptide that performs the same or essentially the same function, preferably binding, compared with the initial polypeptide (for example, functional FimG or FimGt and/or DsF or length variants thereof that bind to each other), and exhibits an amino acid sequence identity of at least 80%, preferably at least 90%, and more preferred of at least 95%.

In formula III, Y is absent or designates at least one of a linker sequence, a detectable peptide sequence and/or a peptide sequence for purifying said polypeptide chain. In formula IV, Y(POI) is absent or designates at least one of a branched linker sequence having POI attached thereto, a detectable peptide sequence and/or a peptide sequence for purifying said polypeptide chain.

Linkers are short peptide sequences that occur between protein domains. e.g. fused domains. Preferred are branched or unbranched peptide linker sequences, such as a branched or unbranched glycine or glycine/serine containing peptide linker sequence Usually, linker sequences are introduced in order to connect and/or to provide a space between functional elements of a polypeptide construct. Linkers are often composed of flexible residues like glycine and serine so that the adjacent protein domains are free to move relative to one another. Longer linkers are used when it is necessary to ensure that two adjacent domains do not sterically interfere with one another. Peptide linker sequences may also include cleavable (e.g. peptidase or chemically cleavable) linkers. Suitable linkers can be designed based on the literature and the skill of the person in the art (see, for example, Chen X, Zaro J L, Shen W C. Fusion protein linkers, property, design and functionality. *Adv Drug Deliv Rev.* 2013, 65(10)-1357-1369 doi:10.1016/j.addr.2012.09.039; Joshua S. Klein, Siduo Jiang, Rachel P. Galimidi, Jennifer R. Keeffe, Pamela J. Bjorkman, Design and characterization of structured protein linkers with differing flexibilities. *Protein Engineering, Design and Selection*, Volume 27, Issue 10, October 2014, Pages 325-330, https://doi.org/10.1093/protein/gzu043). As an example as described below, a polymerase gene is fused to the truncated pIII protein via a 23 amino acid long linker. WO/1998/019705 discloses branched peptide linkers. Similarly, suitable branched linkers can also be designed based on the literature and the skill of the person in the art (see, for example, Brunetti, J, Falciani, C, Bracci, L, Pini, A.

Branched peptides as bioactive molecules for drug design. *Pept Sci.* 2018, 110:e24089. https://doi.org/10.1002/pep2.24089).

Detectable peptide sequences (also designated as tags or markers) allow for the identification of said peptide sequences, and, as a consequence, of the whole fusion construct or the part thereof comprising said sequence(s). Some detectable sequences may also be used to (affinity) purify said fusion construct or the part thereof comprising said sequence. Examples are the myc-tag or the Tie2-tag to be detected with respective antibodies, other antigen markers (see, for example, Hopp, T., Prickett, K., Price, V. et al. A Short Polypeptide Marker Sequence Useful for Recombinant Protein Identification and Purification. *Nat Biotechnol* 6, 1204-1210 (1988). https://doi.org/10.1038/nbt1088-1204), chelator groups (metals, radionuclides), or fluorophore groups.

Peptide sequences for purifying the polypeptide chain of the whole fusion construct or a part thereof comprising said sequence(s) are described in the literature and known to the person of skill in the art Examples are sequences that may be used to (affinity) purify said polypeptide chain (see, for example, Kimple M E, Brill A L, Pasker R L. Overview of affinity tags for protein purification. *Curr Protoc Protein Sci.* 2013; 73:9.9.1-9.9.23. Published 2013 Sep. 24 doi:10.1002/0471140864.ps0909s73), a calmodulin binding peptide, a His-tag, such as a 6 His-tag, and/or maltose binding protein sequence.

In formula IV, POI designates a protein of interest. In the polypeptide chain according to the present invention, PO can be selected from the group consisting of enzymes, antibodies and fragments thereof, such as scFvs, Fab, polymerases, such as nucleic acid polymerases, cytokines, and functional fragments thereof, and libraries or panels thereof. Preferred are antibodies and fragments thereof, nucleic acid polymerases or enzymes that cleave or modify a substrate or ligand, preferably SUB (see below), either alone or in the context with other proteins, e.g. to be screened (see also below) The cleaved or modified substrate may be detected further.

In formula IV, CPF designates a coat protein of a filamentous phage, preferably a minor coat protein. Examples are selected from minor coat proteins of phage fd, M13, f1, and Pf1, such as pIII, pVI, pVII, pVIII, pIX, and truncated versions thereof capable of functionally replacing the respective coat protein of a filamentous phage.

Finally, in formula III, SUB designates a substrate that can be cleaved or modified, either by the POI(s) alone or in the context with other proteins, e.g. proteins to be screened (see also below) or a ligand. The cleaved or modified substrate may be detected further SUB can be selected from the group consisting of a substrate for an enzyme, a ligand, e.g. for POL, a cleavable detectable marker (comprising metal, a fluorophore, a quencher), an antigen marker, and libraries thereof.

Preferred is the protein complex according to the present invention, wherein said complex is stabilized or essentially stabilized through donor strand complementation between the independent contiguous polypeptide sequences of formula I and II, and formula III and IV, respectively.

Yet another aspect of the present invention relates to a filamentous phage displaying at least one protein of interest (PO) as disclosed herein, comprising the protein complex according to the present invention. Preferably, said filamentous phage is selected from fd, M13, f1, and Pf1. More preferably, in said filamentous phage CPF replaces or at least partially replaces a coat protein of said filamentous phage, preferably a minor coat protein thereof, more preferably the respective native minor coat protein, and most preferably capable of functionally replacing the respective coat protein of said filamentous phage.

Yet another aspect of the present invention relates to a library of the filamentous phage according to the present invention, displaying variants of POI and/or the substrate or ligand (SUB).

Still another aspect of the present invention relates to a bacterial host cell comprising the filamentous phage according to the present invention or bacterial host cells comprising the library of the filamentous phage according to the present invention Preferable host cells are *E. coli*, or *Pseudomonas aeruginosa.*

Another aspect of the present invention relates to a nucleic acid encoding for the first (formula I) or second (formula II) polypeptide chain of the protein complex according to the present invention, or a nucleic acid encoding for the first (formula III) or second (formula IV) polypeptide chain of the protein complex according to the present invention. The nucleic acid can be DNA, RNA, PNA or mixtures thereof. Yet another aspect of the present invention relates to a bicistronic nucleic acid encoding the first (formula I) and second (formula II) polypeptide chain of the protein complex according to the present invention, or a bicistronic nucleic acid encoding the first (formula III) and second (formula IV) polypeptide chain of the protein complex according to the present invention. Preferred is the nucleic acid according to the present invention, comprising and encoding variants of POI and/or SUB. Another aspect of the present invention relates to a library of nucleic acids according to the present invention. Included are also expression constructs and vectors comprising and expressing a nucleic acid/nucleic acids according to the present invention.

Another aspect of the present invention relates to a phagemid (see, for example, Qi H, Lu H, Qiu H J, Petrenko V, Liu A. Phagemid vectors for phage display: properties, characteristics and construction. *J Mol Biol.* 2012, 417(3) .129-143. doi:10.1016/j.jmb.2012.01.038), comprising a nucleic acid encoding for the first (formula I) and second (formula 11) polypeptide chain or a nucleic acid encoding for the first (formula 111) and second (formula IV) polypeptide chain of the protein complex according to the present invention. Another aspect of the present invention relates to a library of phagemids comprising nucleic acids according to the present invention. Preferably, in said phagemid CPF replaces or at least partially replaces a coat protein of a filamentous phage, preferably a minor coat protein thereof, more preferably the respective native minor coat protein, and most preferably capable of functionally replacing the respective coat protein of said filamentous phage.

Still another aspect of the present invention relates to a bacterial host cell comprising the phagemid according to the present invention or bacterial host cells comprising the library of the phagemids according to the present invention. Preferable host cells are *E. coli*, or *Pseudomonas aeruginosa*. In an embodiment the phagemid-transformed bacterial cell produces the structural proteins of a filamentous phage. In a further embodiment the phagemid-transformed bacterial cell replicates single-stranded phagemid DNA in yet another embodiment the phagemid-transformed bacterial cell secretes filamentous phage with the phagemid DNA.

Still another aspect of the present invention relates to a method for producing a phagemid according to the present invention, comprising providing a suitable phagemid vector, and inserting a nucleic acid according to the present invention into said vector. Yet another aspect of the present invention relates to a method for producing a library of phagemids according to the present invention, comprising providing suitable phagemid vectors, and inserting a library of nucleic acids according to the present invention into said phagemid vectors.

Still another aspect of the present invention relates to a method for producing a filamentous phage according to the present invention, comprising suitably inserting a nucleic acid according to the present invention into the genome of a suitable filamentous phage, and optionally expressing said genome in a suitable host bacterium. Yet another aspect of the present invention relates to a method for producing a library of filamentous phages according the present invention, comprising inserting a library of nucleic acids according to the present invention into genomes of a suitable filamentous phage, and optionally expressing said genomes in a suitable host bacterium. Preferably, in said filamentous phage or library of filamentous phages CPF replaces or at least partially replaces a coat protein of said filamentous phage(s), preferably a minor coat protein thereof, more preferably the respective/corresponding native minor coat protein, and most preferably capable of functionally replacing the respective coat protein of said filamentous phage.

Another important aspect of the present invention relates to a method for screening for a protein of interest (P01) that specifically interacts with at least one substrate or ligand (SUB), comprising a) Providing a library of filamentous phages according the present invention,
b) Contacting said at least one substrate or ligand with said library of a),
c) Determining an interaction, preferably a specific interaction, of said substrate or ligand with said library, and
d) Identifying a P01 based on said interaction, preferably said specific interaction.

Preferred is the method according to the present invention, wherein said POI is an antibody or fragment thereof as described herein. Preferred is the method according to the present invention, wherein said POI is a polymerase or truncated version thereof as described herein.

Phage display is a powerful technique for studying protein-ligand interactions most frequently applied to protein-protein, protein-peptide, and protein-nucleic acids interactions. The genetic code for the protein/peptide of interest is inserted in the genome of a phage and subsequently "displayed" on the surface of the viral particle as a fusion to natural coat protein. Libraries of protein/peptide variants are tested against ligand(s) of interest Proteins/peptides binding to the specific target are selected by 3-5 rounds of affinity-driven biopanning and subsequently identified by sequencing the genome of the phages displaying them. Phage display is widely used for a selection of proteins/peptides with desired binding properties for the purpose of a broad array of therapeutic, research, and nanotechnology-related applications (see, for example, Boriana Marintcheva, Harnessing the Power of Viruses, Academic Press, 2018, Chapter 5, Pages 133-160, ISBN 9780128105146, https://doi.org/10.1016/B978-0-12-810514-6.00005-2).

Preferably, the method for screening comprises biopanning. In brief, in a preferred embodiment, biopanning is an affinity selection technique which selects for peptides that bind to a given target. The technique is often used for the selection of antibodies. Biopanning involves four major steps for peptide selection. The first step is to provide a phage display library. The next step is the capturing step. It involves conjugating the phage library to the desired target. This procedure is termed panning. It utilizes the binding interactions so that only specific peptides presented by bacteriophage are bound to the target. For example, selecting antibody presented by bacteriophage with coated antigen in microtiter plates. The washing step comes after the capturing step to wash away the unbound phages from solid surface. Only the bound phages with strong affinity are kept. The final step involves the elution step where the bound phages are eluted through changing of pH or other environment conditions. The end result is the peptides produced by bacteriophage are specific. The resulting filamentous phages can infect gram-negative bacteria once again to produce phage libraries. The cycle can occur many times resulting with strong affinity binding peptides to the target. The process can be at least partially automated, for example using robots.

Another aspect of the present invention relates to the use of the protein complex according to the present invention, the nucleic acid(s) according to the present invention or the library of nucleic acids according to the present invention for producing phagemids or filamentous phages.

The present invention makes use of the infinite kinetic stability of the bacterial pilus protein complex FimGt-DsF, which shows an extrapolated dissociation half-life of $3\times10^9$ years (Puorger et al., Structure 2008, 16, 631). Using FimGt-DsF for phage display overcomes the above described limitations of conventional phage display by providing an extremely stable and specific linkage that enables 1) attachment of the PO via its N-terminus, 2) independent translocation of the POI and phage protein with combinations of signal sequences for the different secretion pathways, and 3) the attachment of substrates for the directed evolution of bond-forming and bond-breaking enzymes.

The present invention particularly relates to the following Items.

Item 1. A protein complex comprising a) a first polypeptide chain having the general formula (I) in N- to C-terminal direction X-DsF-Y-POI (I), and b) a second polypeptide chain having the general formula (II) in N- to C-terminal direction X-FimGt-Y-CPF (II), wherein X is absent or designates a bacterial leader sequence or translocation sequence, DsF designates a bacterial DsF-polypeptide required for binding to FimGt or a bacterial homolog thereof, Y is absent or designates at least one of a linker sequence, a detectable peptide sequence and/or a peptide sequence for purifying said polypeptide chain, POI designates a protein of interest, FimGt designates a bacterial FimGt-polypeptide required for binding to DsF or a bacterial homolog thereof, and CPF designates a coat protein of a filamentous phage.

Item 2. A protein complex comprising a) a first polypeptide chain having the general formula (III) in N- to C-terminal direction X-SUB-DsF-Y (III), and b) a second polypeptide chain comprising at least one POI and having the general formula (IV) in N- to C-terminal direction X-FimGt(POI)-Y(POI)-CPF (IV), wherein X is absent or designates a bacterial leader sequence or translocation sequence, DsF designates a bacterial DsF-polypeptide required for binding to FimGt or a bacterial homolog thereof, Y(POI) is absent or designates at least one of a branched linker sequence having POI attached thereto, a detectable peptide sequence and/or a peptide sequence for purifying said polypeptide chain, POI designates a protein of interest, FimGt(POI) designates a bacterial FimGt-polypeptide required for binding to DsF or a bacterial homolog thereof, optionally having POI linked thereto, SUB designates a substrate, and CPF designates a coat protein of a filamentous phage.

Item 3 The protein complex according to Item 1 or 2, wherein said bacterial leader or translocation sequence is selected from a leader sequence for secretion by a secretion pathway or a translocation sequence for translocation by a translocation system, such as, for example, PelB, DsbA, TorA, and PhoA, and the general secretion (Sec) pathway, twin arginine translocation (Tat) pathway, T2SS pathway, T3SS pathway, T5SS pathway, and SecA2 pathway.

Item 4. The protein complex according to any one of Items 1 to 3, wherein said bacterial DsF- and FimGt polypeptides are derived from *E. coli* or are selected from homologs of DsF and/or FinGt derived from a Gram-negative bacterium, in particular of an Enterobacteriaceae.

Item 5 The protein complex according to any one of Items I to 4, wherein Y is selected from a branched or unbranched peptide linker sequence, such as a branched or unbranched glycine or glycine/serine peptide linker sequence, a myc-tag and a Tie2-tag as detectable peptide sequence and/or a calmodulin binding peptide, a His-tag or maltose protein binding sequence for purifying said polypeptide chain.

Item 6. The protein complex according to any one of Items I to 5, wherein said complex is stabilized or essentially stabilized through donor strand complementation between the independent contiguous polypeptide sequences of formula I and II, and formula III and IV, respectively.

Item 7. The protein complex according to any one of Items 1 to 6, wherein CPF is selected from minor coat proteins of phage fd, M13, f1, and Pf1, such as pIII, pVI, pVII, pVIII, pIX, and truncated versions thereof capable of functionally replacing the respective coat protein of a filamentous phage.

Item 8. The protein complex according to any one of Items 1 to 7, wherein PO is selected from the group consisting of enzymes, antibodies, and nucleic acid polymerases, and functional fragments thereof, and libraries thereof.

Item 9. The protein complex according to any one of Items 1 to 8, wherein SUB is selected from the group consisting of a substrate for an enzyme, a cleavable detectable marker, an antigen market, and libraries thereof.

Item 10. A filamentous phage displaying at least one protein of interest (POI), comprising the protein complex according to any one of Items t to 9.

Item 11. The filamentous phage according to item 10, wherein said filamentous phage is selected from fd, M13, f1, and Pf1.

Item 12. A library of the filamentous phage according to item 10 or 11, optionally displaying variants of POI and/or the substrate (SUB).

Item 13. A nucleic acid encoding for the first or second polypeptide chain of the protein complex according to any one of Items I to 9, or a nucleic acid encoding for the first or second polypeptide chain of the protein complex according to any one of Items 2 to 9.

Item 14. A bicistronic nucleic acid encoding the first and second polypeptide chain of the protein complex according to any one of items 1 to 9, or a bicistronic nucleic acid encoding the first and second polypeptide chain of the protein complex according to any one of Items 2 to 9.

Item 15. The nucleic acid according to Item 13 and/or 14, comprising variants of POI and/or SUB.

Item 16. A library of nucleic acids according to any one of Items 13 to 15.

Item 17. A phagemid comprising a nucleic acid according to any of Items 13 to 15 or a library of phagemids comprising nucleic acids according to Item 16.

Item 18. A method of producing a phagemid according to Item 17, comprising providing a suitable phagemid vector, and inserting a nucleic acid according to any one of items 13 to 15 into said vector.

Item 19. A method of producing a library of phagemids according to Item 17, comprising providing suitable phagemid vectors, and inserting a library of nucleic acids according to Item 16 into said vectors.

Item 20. Method of producing a filamentous phage according to Item 10 or 11, comprising inserting a nucleic acid according to any one of Items 13 to 15 into the genome of a suitable filamentous phage, and optionally expressing said genome in a suitable host bacterium.

Item 21. Method of producing a library of filamentous phages according to Item 12, comprising insetting a library of nucleic acids according to Item 16 into genomes of a suitable filamentous phage, and optionally expressing said genomes in a suitable host bacterium.

Item 22. Method for screening for a protein of interest (P01) that specifically interacts with a substrate or ligand, comprising a) Providing a library according to Item 12, b) Contacting said substrate or ligand to said library of a), c) Determining an interaction, preferably a specific interaction, of said substrate or ligand with said library, and d) Identifying a P01 based on said interaction, preferably said specific interaction.

Item 23 The method according to Item 22, wherein said POI is an antibody or fragment thereof, and said method comprises biopanning.

Item 24. The method according to item 22, wherein said POI is a polymerase or truncated version thereof.

Item 25. Use of the protein complex according to any one of Items I to 9, the nucleic acid according to any one of Items 13 to 15 or the library of nucleic acids according to claim 16 for producing phagemids or filamentous phages.

The present invention will now be described further in the following examples with reference to the accompanying Figures, nevertheless, without being limited thereto. For the purposes of the present invention, all references as cited herein are incorporated by reference in their entireties.

FIG. 1 shows schematic examples of the use of FimGt-DsF for phage display. (A) FimGt-DsF enables the POI to be linked to the phage via its N-terminus and to be independently translocated from the phage coat protein with different combinations of secretion pathways. (B) FimGt further provides an anchor for the attachment of DsF tagged substrates allowing evolution of bond-forming and bond-breaking enzymes.

Figure 2:
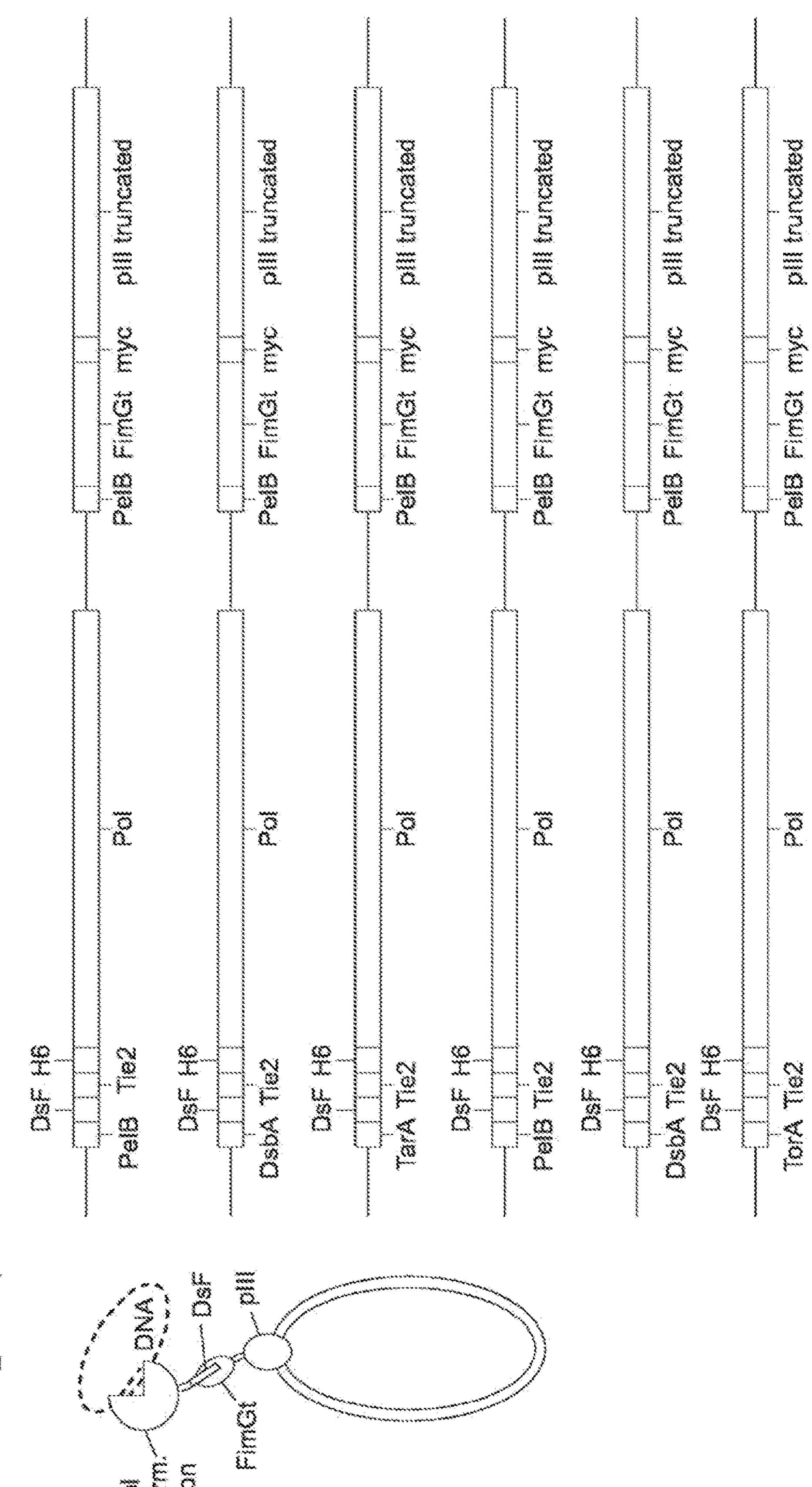
Figure 2:
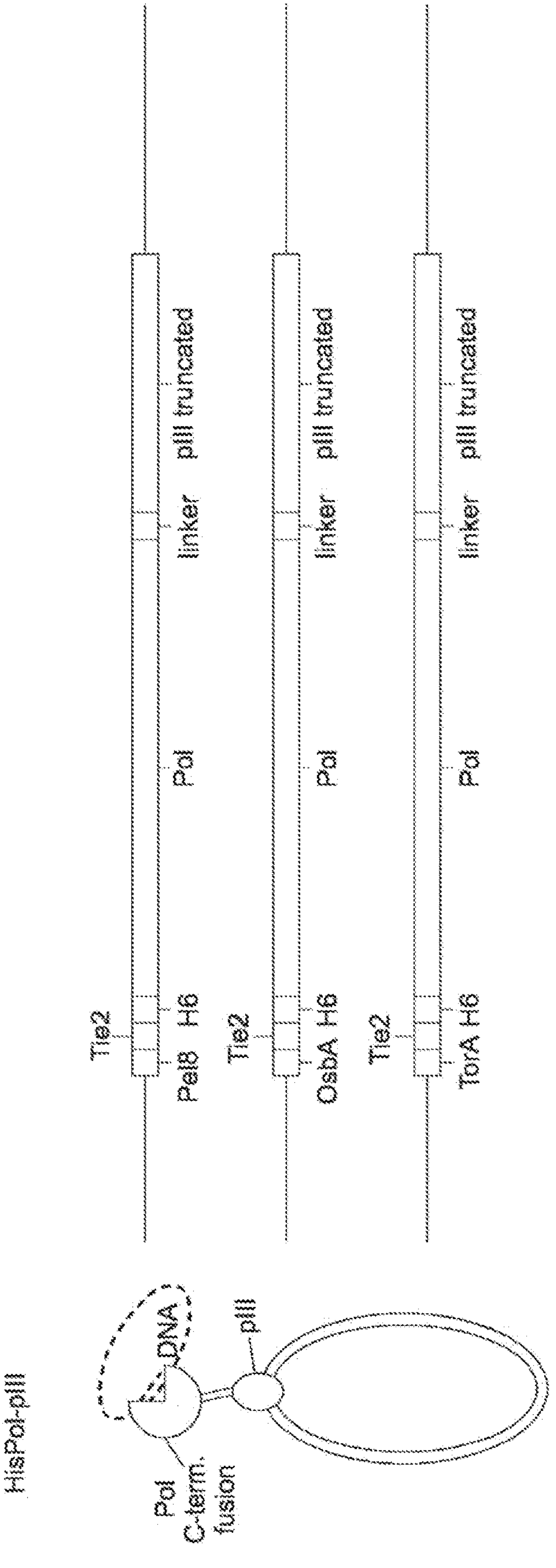

FIG. 2 shows phage display constructs. (Top) The Fim phagemid constructs for display of the DNA polymerase from *Clostridium* phage phiCPV4 (Pol) via N-terminal attachment contain the biscistronic arrangement of the polymerase gene fused to the DsF peptide at its N-terminus and the FimGt gene fused to the N-terminus of truncated pIII (pIIIt, residues 250-406). A His6-tag is inserted at the N-terminus of the Pol for purification and a Tie2 tag for detection. The FimGt-pIII fusion contains a myc tag between FimGt and truncated pIII for detection. Versions with six different combinations of signal sequences were constructed: For the polymerase the PelB signal sequence of *Erwinia carolovora* pectate lyase B to facilitate translocation via the Sec pathway, the DsbA signal sequence of *E. coli* thioldisulfide interchange protein DsbA to facilitate translocation via the SRP pathway, and the TorA signal sequence of *E. coli* trimethylamine-N-oxide reductase to facilitate translocation via the Tat pathway, were cloned and combined with either PelB or DsbA signal sequence for the translocation of the FimGt-pIII fusion protein (Bottom) For the classical phagemid constructs the polymerase gene is fused to the truncated pIII via a 23 amino acid long linker. Like in the Fim constructs, a His6-tag is inserted at the N-terminus of the Pol for purification and a Tie2 tag for detection. Versions with the three signal sequences PelB, DsbA, and TorA for translocation of the Pol-pIII fusion protein via the three different pathways were constructed.

Figure 3:
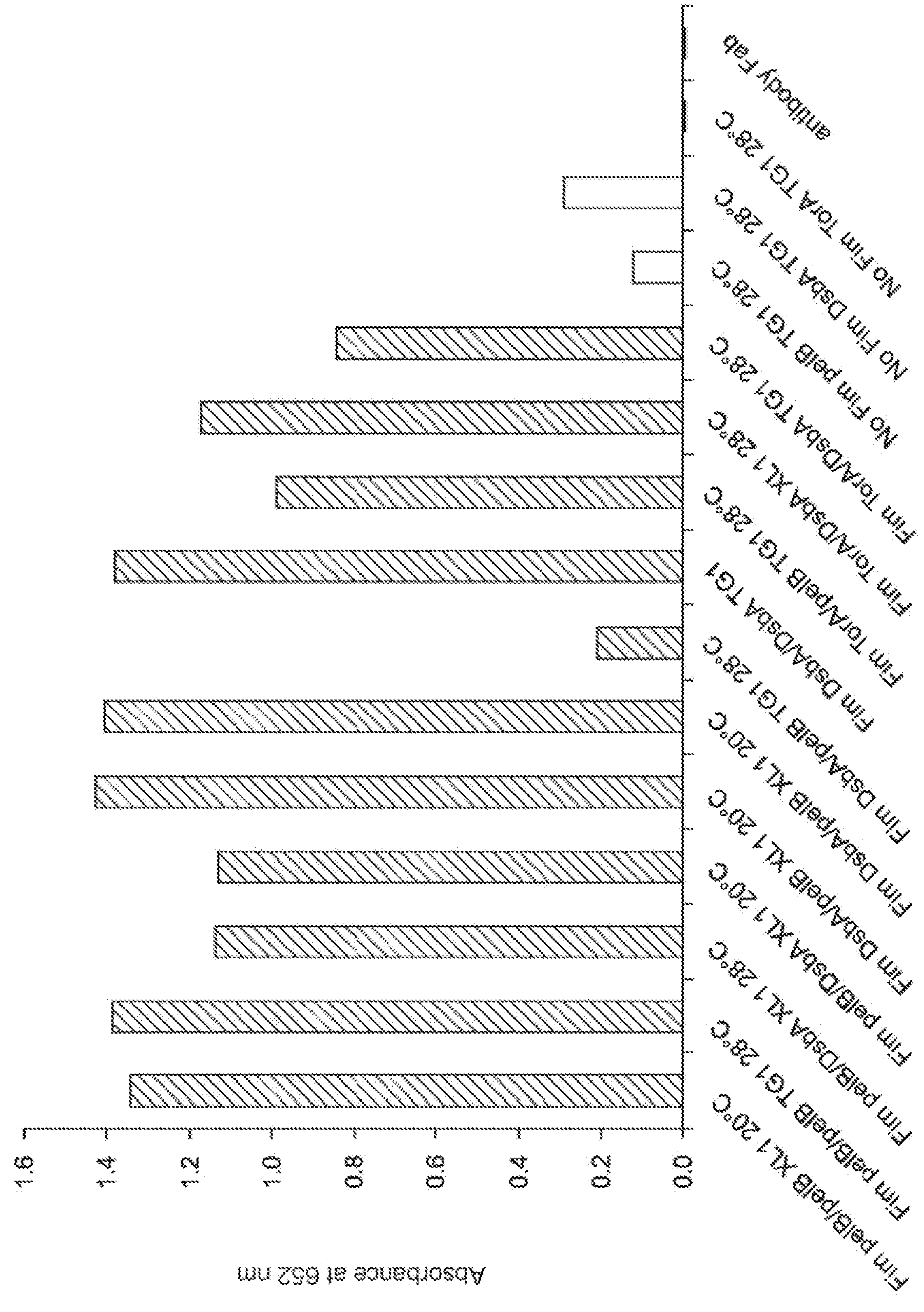

FIG. 3 shows phage ELISA of polymerase displaying phages. The display level of phage samples having the polymerase attached via FimGt-DsF (dark gray, Fim) or direct fusion (gray, no Fim) and expressed under different conditions are compared. The signal sequences used for the Pol fusion and the FimGt fusion protein are indicated, as well as the host strain XII-Blue (XL1) or TG1, and the expression temperature. For each preparation the titer was determined and 109 phages were used per well. The signal (absorbance at 652 nm) of the helper phage M13KO7 was subtracted from the signals of all samples. The Fab displaying phages do not exhibit any signal after subtraction, indicating that the signal in this phage EISA is specific to polymerase displaying phages.

Figure 4:
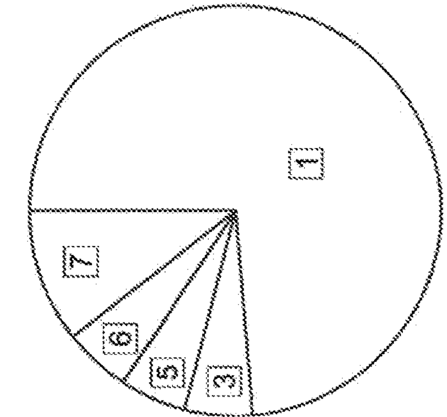
Figure 4:
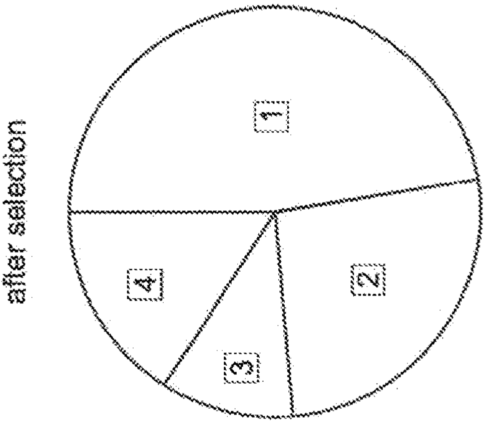
Figure 4:
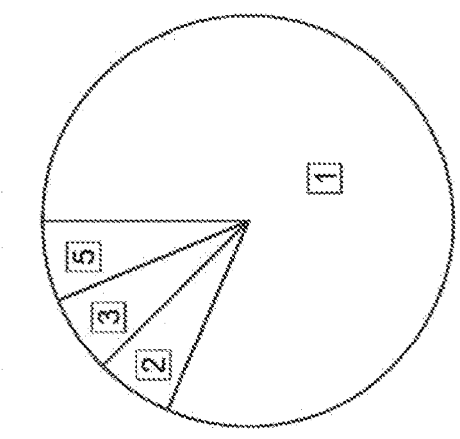

FIG. 4 shows model selections of polymerase displaying phages for DNA binding. Phages displaying the polymerase via FimGt-DsF (Fim) or direct fusion (No Fim) from the preparations listed in Table 1 were mixed at equal amounts and an estimated amount of 60 to 75% antibody Fab displaying phages was added. The phage mixture was selected for DNA binding to a primer template complex immobilized via biotin on streptavidin magnetic beads. A control selection was performed with streptavidin beads that had no DNA bound. The identity of 20 phages before selection (left), and after selection (middle) or control selection (right) was determined by infection of TG1 cells and sequence analysis of the phagemids.

EXAMPLES

Materials and Methods

Materials

Buffers and salts were purchased from commercial suppliers. Oligonucleotides were from IDT. Restriction enzymes and DNA polymerases were from Roche, New England Biolabs or Agilent (Stratagen). Antibodies were obtained from the following suppliers: mouse anti-M13 pIII (NEB), rabbit anti-mouse-HRP (Invitrogen), goat anti-rabbit-HRP (Invitrogen), mouse anti-M13-HRP (GE Healthcare). Rabbit anti-Tie2 monoclonal antibody is a Roche-internal research tool (not commercially available) *E. coli* strains XII-Blue and X110-Gold were from Agilent (Stratagene) and TG1 was from Lucigen. Helper phage M13KO7 was from GE Healthcare. Unless stated otherwise, microbiological and molecular biological methods were performed according to standard procedures (J. Sambrook, D. Roulland, Molecular Cloning: A Laboratory Manual., Cold Spring Harbor Laboratory Press, Cold Spring Harbor, N Y, 2001).

Cloning

The inserts of the phagemids pETR-DsF-HisPol6_FimGt-pIII and pETR-HisPol6-pIII were assembled by overlap extension PCR using primers containing linkers and tags, and the genes of DNA polymerase from *Clostridium* phage phiCPV4 (Pol6, see WO 2017/148862), FimGt and M13 minor coat protein pIII as templates. The PCR products were cloned into pETR phagemid (vector from Roche Glycart). The PelB signal sequence was exchanged by PCR with primers containing the DsbA or TorA sequences and subsequent cloning into the pETR phagemids.

Phage Production and Purification

XL1-Blue and TG1 cells were transformed with the phagemids. Single colonies were used to inoculate pre-cultures in 2×YT medium (5 ml) supplemented with 1% glucose and 100 μg/ml ampicillin and incubated overnight at 30° C. with shaking. The pre-cultures were used to inoculate cultures in 50 ml fresh 2×YT medium containing 1% glucose and 100 μg/ml ampicillin at a ratio of 1:100. Cultures were grown at 37° C. to an $OD_{600}$ of 0.5-0.7, then infected with 50 μl helper phage M13KO7 (1013 pfu/ml) and incubated for 45 min at 37° C. with slight agitation. The medium was changed by harvesting the cells by centrifugation at 3320 g and 4° C. for 10 min and resuspension of the pellet in 50 ml of 2×YT medium containing 100 μg/mi ampicillin, 50 μg/mi kanamycin and for the +IPTG samples 0.1 mM isopropyl-β-D-thiogalactoside (IPTG). After growth for 16 h at 28° C. or 24 h at 20° C. and 250 rpm, the cells were removed by centrifugation at 4800 g and 4° C. for 30 min. The supernatant was mixed with one-fourth volume of ice-cold PEG/NaCl solution (20% polyethyleneglycol (PEG) 6000, 2.5 M NaCl) and incubated on ice for 1 h. The precipitated phage particles were pelleted by centrifugation at 7164 g and 4° C. for 30 min. Each pellet was resuspended in 40 ml of washing buffer (50 mM Tris, pH 7.5, 200 mM NaCl, 5 mM DTT) and 10 ml of ice-cold PEG/NaCl solution (20% PEG 6000, 2.5 M NaCl) was added. After incubated on ice for 1 h the phages were collected by centrifugation at 7164 g and 4° C. for 30 min and the pellets each were resuspended in 1.6 ml pol storage buffer (50 mM Tris, pH 7.5, 200 mM NaCl, 0.5% Tween 20, 25% glycerol, 5 mM DTT). To discard any bacterial debris the phages were centrifuged at 16100 g and 4° C. for 3 min. The infective titer of the phage samples was determined by infection of *E. coli* TG1 cells and titration on 2×YT agar plates containing 1% glucose and 100 μg/ml ampicillin.

Western Blot Analysis

Purified phage samples were supplemented with SDS loading dye and reductant. SDS-PAGE was carried out on 4-12% Bis-Tris gels (Invitrogen), and was followed by transfer onto nitrocellulose membranes using the iBlot dry blotting system (invitrogen). Phage minor coat protein pIII and its fusions were detected using a mouse anti-M13 pIII at a dilution of 1:10000 as the primary antibody and a horseradish peroxidase-conjugated rabbit anti-mouse IgG antibody diluted 1:2000 as the secondary antibody. The polymerase was detected by the Tie2 tag using a rabbit anti-Tie2 antibody at a dilution of 1:2500 as the primary antibody and a horseradish peroxidase-conjugated goat anti-rabbit IgG antibody diluted 1-2000 as the secondary antibody Blots were developed with the Lumi-Light substrate from Roche.

Phage ELISA

Rabbit anti-Tie 2 was coated at a concentration of 2.5 μg/ml onto Immunomaxi 96 well plates (Thermo Fisher) as capture antibody. After blocking and washing, 109 phage particles per well (determined by titration) were added to the wells and incubated for 1 h at RT After washing, bound phage were detected with horseradish peroxidase-conjugated mouse anti-M13 antibody (GE Healthcare), diluted 1:2500. The plates were developed using the Pierce™ TMB (3,3',5,5'tetramethylbenzidine) Substrate Kit (Thermo Fisher) and detection of the absorption at 370 and 652 nm.

Model Selections

Phage particles from the nine phagemid constructs with and without FimGt-DsF produced under the different conditions listed in Table 1 (72 preparations) were mixed at equal volumes. Phages displaying an antibody Fab fragment were added to the polymerase displaying phage mixture at an amount estimated by the western blots to account for 60% to 75% of total phages in the mixture. The phage mixture was PEG precipitated (see phage production and purification section) once and resuspended in pol binding buffer (50 mM Tris, pH 7.5, 55 mM glutamate. 0.1% Tween 20, 1% BSA, 5 mM DTT). Freshly centrifuged phages were added to streptavidin magnetic beads (Dynabeads M2-80 Streptavidin, Invitrogen) that had been blocked with BSA, coated with a biotinylated primer template complex, and then incubated with biotin to saturate remaining free streptavidin binding sites. Control beads were not coated with the biotinylated primer template complex but otherwise treated the same. Phages were incubated on the beads for 20 min at RT, unbound phages were washed away, and bound phages were eluted by incubation with DNase (20 U/100 μl beads) tor 1 h at RT Exponentially growing TG1 cells were infected with the recovered phages and with an aliquot of the phage mixture before selection. After incubation for 30 min at 37° C. with slight agitation dilutions of the cells were plated on 2×YT agar plates containing 1% glucose and 100 μg/ml ampicillin to determine the titer and to obtain colonies for determination of the identity of the phages. The identity of 20 phagemids each was determined by sequencing.

N-Terminal Attachment of a DNA Polymerase Via FimGt-DsF Enables Functional Display on the Filamentous Phage M13

Design and Cloning of the Phage Display Constructs

In this example the inventors used FimGt-DsF in order to display the DNA polymerase from *Clostridium* phage phiCPV4 via N-terminal attachment to the phage. When fused at its C-terminus, this polymerase greatly loses activity. Therefore, N-terminal fusion should be crucial for the display of active polymerase.

For N-terminal attachment of the polymerase to the phage, the polymerase was cloned biscistronically into the phagemid vector in front of the FimGt-pIII fusion protein (FIG. 2, top). The DsF peptide was then linked to the N-terminus of the polymerase, and a his tag for purification, and a Tie2 tag for detection with anti-Tie2 antibody were included. FimGt was fused to truncated minor coat protein pIII, and a myc tag was added for detection. In addition to the standard PelB leader sequence for secretion by the Sec pathway constructs with DsbA and TorA signal sequences for translocation of the polymerase by the SRP and Tat pathway, respectively, were cloned and combined with either PelB or DsbA for translocation of the FimGtDsF fusion (since FimGt is naturally secreted to the periplasm and folds and assembles there, the Tat pathway was not considered). For comparison, classical phage display constructs without FimGt-DsF but direct fusion of the polymerase via its C-terminus to the pIII coat protein were designed and cloned (FIG. 2, bottom). As for the FimGt-DsF construct, versions with the signal sequences PelB, DsbA, and TorA were constructed for translocation of the polymerase-pIII fusion via the different secretion pathways.

Phage Production in Several *E. coli* Strains and Under Different Conditions

To find optimal conditions for the production of the two polymerase-displaying phage constructs *E. coli* strains TG1 and XII-Blue were tested as well as expression temperatures of 28° C. and 20° C., and usage of medium with and without IPTG after helper phage infection.

Assessment of Phage Production and Display by Western Blot

The results of phage production under the various conditions described above were evaluated by western blot (Table 1). Total phage production is reflected by the amount of pIII protein, which is detected by a monoclonal anti-pIII antibody Display levels can be assessed by the amount of pIII fusion protein (FimGt-pIII or polymerase-pIII) detected by the same monoclonal anti-pIII antibody and by detection of the DsF-polymerase or polymerase-pIII proteins using the Tie2 tag and an anti-Tie2 antibody. The amounts of the different proteins in the western blots were evaluated visually and rated from not detectable (−) to strong band (+++). The results are summarized in Table 1 and show that while both the Fim constructs and the classical constructs produce phages, the Fim constructs, which have the polymerase attached via its N-terminus, generally show higher display levels. IPTG addition to the growth medium tends to yield lower phage amounts and display levels suggesting that a strong induction of polymerase and pill fusions is disadvantageous. Best host strain and expression temperature varied between constructs. The polymerase constructs showed no preference for a specific combination of signal sequences.

TABLE 1

Determination of phage production and display by Western blot

| Conditions | | | | | Results | | |
|---|---|---|---|---|---|---|---|
| | | | | | Phage production by | Display levels by | Display levels by |
| construct | Signal sequence | *E. coli* strain | Expression temperature | IPTG | detection of pIII | pIII fusion | detection of Pol |
| His-Pol-DsF_FimGt-pIII | PelB/PelB | XL1-Blue | 28° C. | − | + | + | +++ |
| | | | 20° C. | − | ++ | + | +++ |
| | | TG1 | 28° C. | − | +++ | + | ++ |
| | | | 20° C. | − | ++ | + | − |
| | | XL1-Blue | 28° C. | + | − | − | + |
| | | | 20° C. | + | − | − | +++ |

TABLE 1-continued

Determination of phage production and display by Western blot

| Conditions | | | | | Results | | |
|---|---|---|---|---|---|---|---|
| | | | | | Phage production by | Display levels by | Display levels by |
| construct | Signal sequence | *E. coli* strain | Expression temperature | IPTG | detection of pIII | pIII fusion | detection of Pol |
| | | TG1 | 28° C. | + | +++ | | + |
| | | | 20° C. | + | − | − | − |
| | PelB/DsbA | XL1-Blue | 28° C. | − | ++ | + | +++ |
| | | | 20° C. | − | ++ | + | +++ |
| | | TG1 | 28° C. | − | +++ | ++ | − |
| | | | 20° C. | − | ++ | ++ | − |
| | | XL1-Blue | 28° C. | + | − | − | + |
| | | | 20° C. | + | − | − | +++ |
| | | TG1 | 28° C. | + | +++ | + | − |
| | | | 20° C. | + | − | − | − |
| | DsbA/PelB | XL1-Blue | 28° C. | − | +++ | + | +++ |
| | | | 20° C. | − | ++ | ++ | +++ |
| | | TG1 | 28° C. | − | +++ | ++ | + |
| | | | 20° C. | − | +++ | ++ | + |
| | | XL1-Blue | 28° C. | + | +++ | − | +++ |
| | | | 20° C. | + | + | − | − |
| | | TG1 | 28° C. | + | +++ | ++ | − |
| | | | 20° C. | + | + | + | ++ |
| | DsbA/DsbA | XL1-Blue | 28° C. | − | ++ | + | ++ |
| | | | 20° C. | − | ++ | + | + |
| | | TG1 | 28° C. | − | ++ | ++ | ++ |
| | | | 20° C. | − | + | + | + |
| | | XL1-Blue | 28° C. | + | − | − | + |
| | | | 20° C. | + | − | − | + |
| | | TG1 | 28° C. | + | ++ | − | − |
| | | | 20° C. | + | − | − | − |
| | TorA/PelB | XL1-Blue | 28° C. | − | + | + | + |
| | | | 20° C. | − | − | − | − |
| | | TG1 | 28° C. | − | ++ | ++ | + |
| | | | 20° C. | − | +++ | + | − |
| | | XL1-Blue | 28° C. | + | − | − | − |
| | | | 20° C. | + | − | − | − |
| | | TG1 | 28° C. | + | ++ | − | − |
| | | | 20° C. | + | − | − | − |
| | TorA/DsbA | XL1-Blue | 28° C. | − | ++ | + | +++ |
| | | | 20° C. | − | + | + | − |
| | | TG1 | 28° C. | − | +++ | ++ | ++ |
| | | | 20° C. | − | − | − | − |
| | | XL1-Blue | 28° C. | + | − | − | + |
| | | | 20° C. | + | − | − | − |
| | | TG1 | 28° C. | + | +++ | ++ | + |
| | | | 20° C. | + | ++ | + | − |
| HisPol-pIII PelB | PelB | XL1-Blue | 28° C. | − | ++ | − | +++ |
| | | | 20° C. | − | + | − | − |
| | | TG1 | 28° C. | − | +++ | − | ++ |
| | | | 20° C. | − | ++ | − | − |
| | | XL1-Blue | 28° C. | + | − | − | − |
| | | | 20° C. | + | − | − | − |
| | | TG1 | 28° C. | + | +++ | − | + |
| | | | 20° C. | + | − | − | − |
| | DsbA | XL1-Blue | 28° C. | − | +++ | − | + |
| | | | 20° C. | − | ++ | − | − |
| | | TG1 | 28° C. | − | +++ | − | + |
| | | | 20° C. | − | ++ | − | − |
| | | XL1-Blue | 28° C. | + | − | − | − |
| | | | 20° C. | + | − | − | − |

TABLE 1-continued

| Determination of phage production and display by Western blot | | | | | | | |
|---|---|---|---|---|---|---|---|
| | | | | | Results | | |
| Conditions | | | | | Phage production by | Display levels by | Display levels by |
| construct | Signal sequence | *E. coli* strain | Expression temperature | IPTG | detection of pIII | pIII fusion | detection of Pol |
| | | TG1 | 28° C. | + | +++ | − | − |
| | | | 20° C. | + | − | − | − |
| | TorA | XL1-Blue | 28° C. | − | +++ | + | + |
| | | | 20° C. | − | + | − | − |
| | | TG1 | 28° C. | − | +++ | + | + |
| | | | 20° C. | − | +++ | ++ | − |
| | | XL1-Blue | 28° C. | + | +++ | − | − |
| | | | 20° C. | + | − | − | − |
| | | TG1 | 28° C. | + | +++ | − | − |
| | | | 20° C. | + | +++ | + | − |

Proof of Polymerase Display by Phage ELISA

In case of the Fim constructs, two separate fusion proteins, the DsF-polymerase and the FimGt-pIII, are independently translocated to the periplasm and should assemble there. Western blot detection of both fusion proteins thus does not proof their attachment and consequently display of the polymerase on the phage surface. Therefore, a phage ELISA of the phage samples showing highest display by western blot was carried out (FIG. 3). The phage titer of the different samples was determined and ranged from 5×1011 to 3×1013 (cfu/ml). Equal amounts of phages were added to the wells of an ELISA plate and phages displaying the polymerase were captured with the anti-Tie2 antibody, specific for the Tie2 tag on the polymerase. After washing, bound phages were detected with a horseradish peroxidase coupled anti-M13 antibody that birds to the major coat protein pVIII of the phages. Helper phages and phages displaying an antibody Fab fragment served as negative control. The high ELISA signal of the Fim constructs shows that the polymerase is indeed displayed on the phage surface. The ELISA results agree well with the western blot results and the low ELISA signals for the classical constructs without Fim confirm that these constructs display significantly less polymerase suggesting that N-terminal attachment of the polymerase is crucial for display on the phage surface. As seen in the western blots the signal sequence seems to not have an influence on display levels of our polymerase.

The invention claimed is:

1. A protein complex comprising a first polypeptide chain having the general formula (I) in N- to C-terminal direction X-DsF-Y-POI (I), and a second polypeptide chain having the general formula (II) in N- to C-terminal direction X-FimGt-Y-CPF (II), wherein X is absent or designates a bacterial leader sequence or translocation sequence, DsF designates a bacterial DsF-polypeptide comprising the N-terminal extension (donor strand) of bacterial type 1 pilus subunit FimF or a bacterial homolog thereof, wherein said DsF-polypeptide is capable of binding to FimGt, Y is absent or designates at least one of a linker sequence, a detectable peptide sequence and/or a peptide sequence for purifying said polypeptide chain, POI designates a protein of interest, FimGt designates a bacterial FimGt-polypeptide comprising a bacterial type 1 pilus subunit FimG polypeptide or a bacterial homolog thereof, wherein said FimGt-polypeptide is capable of binding to DsF, and CPF designates a coat protein of a filamentous phage.

SEQUENCE LISTING

```
<160> NUMBER OF SEQ ID NOS: 1

<210> SEQ ID NO 1
<211> LENGTH: 10
<212> TYPE: PRT
<213> ORGANISM: artificial sequence
<220> FEATURE:
<223> OTHER INFORMATION: E.coli FimF protein variant peptide

<400> SEQUENCE: 1

Ser Arg Ile Arg Ile Arg Gly Tyr Val Arg
1               5                   10
```

2. A protein complex comprising a first polypeptide chain having the general formula (III) in N- to C-terminal direction X-SUB-DsF-Y (III), and a second polypeptide chain comprising at least one POI and having the general formula (IV) in N- to C-terminal direction X-FimGt(POI)-Y(POI)-CPF (IV), wherein X is absent or designates a bacterial leader sequence or translocation sequence, DsF designates a bacterial DsF-polypeptide comprising the N-terminal extension (donor strand) of bacterial type 1 pilus subunit FimF or a bacterial homolog thereof, wherein said DsF-polypeptide is capable of binding to FimGt, Y(POI) is absent or designates at least one of a branched linker sequence having POI attached thereto, a detectable peptide sequence and/or a peptide sequence for purifying said polypeptide chain, POI designates a protein of interest, FimGt(POI) designates a bacterial FimGt-polypeptide comprising a bacterial type 1 pilus subunit FimG polypeptide or a bacterial homolog thereof, wherein said FimGt-polypeptide is capable of binding to DsF, optionally having POI linked thereto, SUB designates a substrate, and CPF designates a coat protein of a filamentous phage.

3. The protein complex according to claim 1, wherein said bacterial leader or translocation sequence is selected from a leader sequence for secretion by a secretion pathway or a translocation sequence for translocation by a translocation system.

4. The protein complex according to claim 1, wherein said bacterial DsF- and FimGt polypeptides are derived from *E. coli* or are selected from homologs of DsF and/or FimGt derived from a Gram-negative bacterium.

5. The protein complex according to claim 1, wherein Y is selected from a branched or unbranched peptide linker sequence, a myc-tag and a Tie2-tag as detectable peptide sequence and/or a calmodulin binding peptide, a His-tag or maltose protein binding sequence for purifying said polypeptide chain.

6. The protein complex according to claim 1, wherein said complex is stabilized or essentially stabilized through donor strand complementation between the independent contiguous polypeptide sequences of formula I and II.

7. The protein complex according to claim 1, wherein CPF is selected from minor coat proteins of phage fd, M13, f1, and Pf1 and truncated versions thereof capable of functionally replacing the respective coat protein of a filamentous phage.

8. The protein complex according to claim 1, wherein POI is selected from the group consisting of enzymes, antibodies, and nucleic acid polymerases, and functional fragments thereof, and libraries thereof.

9. The protein complex according to claim 2, wherein SUB is selected from the group consisting of a substrate for an enzyme, a cleavable detectable marker, an antigen marker, and libraries thereof.

10. A filamentous phage displaying at least one protein of interest (POI), the filamentous phage comprising the protein complex according to claim 2, wherein said filamentous phage is selected from fd, M13, f1, and Pf1, or a library of said filamentous phage, optionally displaying variants of POI and/or the substrate (SUB).

11. A bicistronic nucleic acid encoding the first and second polypeptide chain of the protein complex according to claim 1.

12. A method for screening for a protein of interest (POI) that specifically interacts with a substrate or ligand, comprising providing the library of said filamentous phage according to claim 10, contacting said substrate or ligand to said library, determining an interaction of said substrate or ligand with said library, and identifying a POI based on said interaction.

13. The method according to claim 12, wherein said POI is an antibody or fragment thereof, and wherein said method comprises biopanning, or wherein said POI is a polymerase or truncated version thereof.

14. The protein complex according to claim 3, wherein the bacterial leader or translocation sequence is selected from PelB, DsbA, TorA, and/or PhoA, and wherein the secretion pathway or translocation system is selected from the general secretion (Sec) pathway, twin arginine translocation (Tat) pathway, T2SS pathway, T3SS pathway, T5SS pathway, and/or SecA2 pathway.

15. The protein complex according to claim 7, wherein CPF is selected from minor coat proteins pIII, pVI, pVII, pVIII, and pIX and truncated versions thereof capable of functionally replacing the respective coat protein of a filamentous phage.

16. The protein complex according to claim 4, wherein the Gram-negative bacterium is Enterobacteriaceae.

17. The protein complex according to claim 5, wherein the branched or unbranched peptide linker sequence is a branched or unbranched glycine or glycine/serine peptide linker sequence.

18. The protein complex according to claim 2, wherein said complex is stabilized or essentially stabilized through donor strand complementation between the independent contiguous polypeptide sequences of formula III and IV.

* * * * *